US006966900B1

(12) United States Patent
Chyba et al.

(10) Patent No.: US 6,966,900 B1
(45) Date of Patent: Nov. 22, 2005

(54) DECONTAMINATION TUB

(75) Inventors: Dennis L. Chyba, Baltimore, MD (US); James M. Hall, Bel Air, MD (US); Patrick J. Richardson, New Market, MD (US); Michael P. Richardson, Frederick, MD (US)

(73) Assignees: Maryland Thermoform Corporation, Baltimore, MD (US); Reeves Manufacturing, Inc., Frederick, MD (US)

( * ) Notice: Subject to any disclaimer, the term of this patent is extended or adjusted under 35 U.S.C. 154(b) by 175 days.

(21) Appl. No.: 10/330,744

(22) Filed: Dec. 26, 2002

Related U.S. Application Data

(60) Provisional application No. 60/344,281, filed on Dec. 27, 2001.

(51) Int. Cl.[7] .............................................. A61M 35/00
(52) U.S. Cl. ...................................................... 604/290
(58) Field of Search ................................ 604/289, 290, 604/293, 318, 408; 4/900, 546, 584, 596; 5/600, 606, 625, 928, 8; 269/289 R, 329, 269/909

(56) References Cited

U.S. PATENT DOCUMENTS

| | | | | |
|---|---|---|---|---|
| 4,713,850 | A | * | 12/1987 | Flaherty et al. ................ 4/585 |
| 4,819,925 | A | * | 4/1989 | Linnemann et al. ........... 5/606 |
| 5,426,795 | A | * | 6/1995 | Harty ............................ 4/584 |
| 5,549,707 | A | * | 8/1996 | Weaver ...................... 604/317 |
| 5,568,817 | A | * | 10/1996 | Harty ........................ 128/849 |
| 6,578,209 | B2 | * | 6/2003 | Lopes et al. ................. 4/572.1 |

FOREIGN PATENT DOCUMENTS

| | | | |
|---|---|---|---|
| EP | 0509292 A1 * | 10/1992 | ............ A61G 7/02 |

* cited by examiner

*Primary Examiner*—Larry I. Schwartz
*Assistant Examiner*—Ginger Chapman
(74) *Attorney, Agent, or Firm*—Armstrong, Kratz, Quintos, Hanson & Brooks, LLP

(57) ABSTRACT

A tub for receiving bodies and/or body parts. The bottom of the tub is sloped to one corner and a drain valve is attached in the one corner of the tub. The body and/or body parts are received in a transfer sheet or stretcher placed in the tub. A decontaminant is provided for application to the body and/or body parts. A method of use is disclosed.

8 Claims, 8 Drawing Sheets

10
12
14
16
18
22
24
26
40
4
6

DECONTAMINATION TUB

CROSS REFERENCE

The present application is related to provisional patent application Ser. No. 60/344,281 filed Dec. 27, 2001.

BACKGROUND OF THE INVENTION

1. Field of the Invention

The present invention is directed to a decontamination tub and more specifically to a decontamination tub for bodies, parts of bodies, blood, body fluids and decontamination medium.

2. Description of Related Art

In the event of an accident, or catastrophe (military or civilian) where persons are killed, there is a need for the bodies and/or body parts to be collected and removed from the scene. This is most commonly done by the rescue personnel placing the body and/or body parts in “body bag”. However, the “body bag” does not effectively contain blood and body fluids and does not provide means to decontaminate the body or body parts when such treatment is required. Decontamination may be needed in the event of exposure to biological and/or chemical agents.

Furthermore, it is sometimes necessary for police, forensic or medical purposes, to store the body, body parts and/or body fluid for subsequent examination. The presently available systems do not provide a convenient means which is rigid and protects the body or body parts and retaining body fluids and decontamination medium.

BRIEF SUMMARY OF THE INVENTION

It is an object of the invention to provide a rigid tub for retention of bodies, body parts and body fluids following a military action, an accident or catastrophic event.

It is a further object of the invention to provide a means to decontaminate bodies and/or body parts.

In accordance with the teachings of the present invention, there is disclosed a tub for receiving a body and/or body parts. Drainage means is provided on the tub for facilitating collection of blood and/or body fluids. A valve means is provided on the tub, so that once the body part or parts are received in the tub, a decontamination medium may be introduced into the tub to decontaminate the body and/or body parts in the tub. The blood and/or body fluids and the decontamination medium may be drained through the valve means.

In further accordance with the teachings of the present invention, there is disclosed a stack of decontamination tubs nested vertically with respect to each other. Each of the decontamination tubs comprises a rigid tub for collection of blood and/or body fluids. A decontamination medium may be introduced into the tub to decontaminate the body and/or body parts in the tub. Each of the tubs has a bottom portion provided with ridges, thereby facilitating movement of the tub along a roller system. Each of the tubs further has four notches, two at each opposite end of the tub, respectively. A stretcher is received in the notches, depending within each tub and having the body and/or body parts resting thereon. A valve means is formed on each tub such that the blood, body fluids and the decontamination medium may be drained through the valve means.

In still further accordance with the teachings of the present invention, there is provided a method of decontaminating bodies and/or body parts following exposure to hazardous materials. A tub having four walls and a bottom is provided. A drain valve is connected to the corner of the tub. The body and/or body parts are placed on a carrying means. The body fluids are collected in the tub. A decontamination medium is connected to a spraying device. The decontamination medium is sprayed onto the body and/or body parts to decontaminate the body and/or body parts. The decontamination medium collects in the tub. The valve in the corner of the tub is opened and the body fluids and decontamination medium drain into a reservoir.

These and other objects of the present invention will become apparent from a reading of the following specification taken in conjunction with the enclosed drawings.

DESCRIPTION OF THE PREFERRED EMBODIMENT

Figure 1:
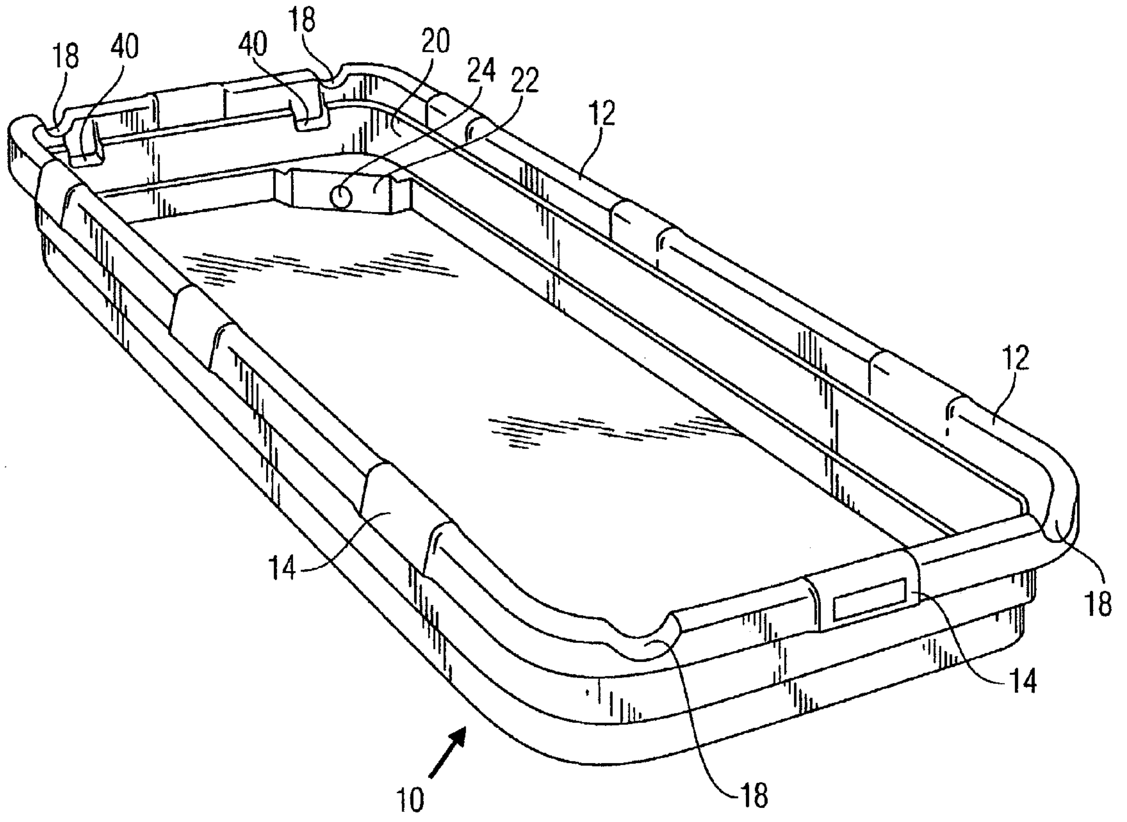
FIG. 1 is a perspective view of the decontamination tub of the present invention.
Figures 2, 3, 4, 5, 6:
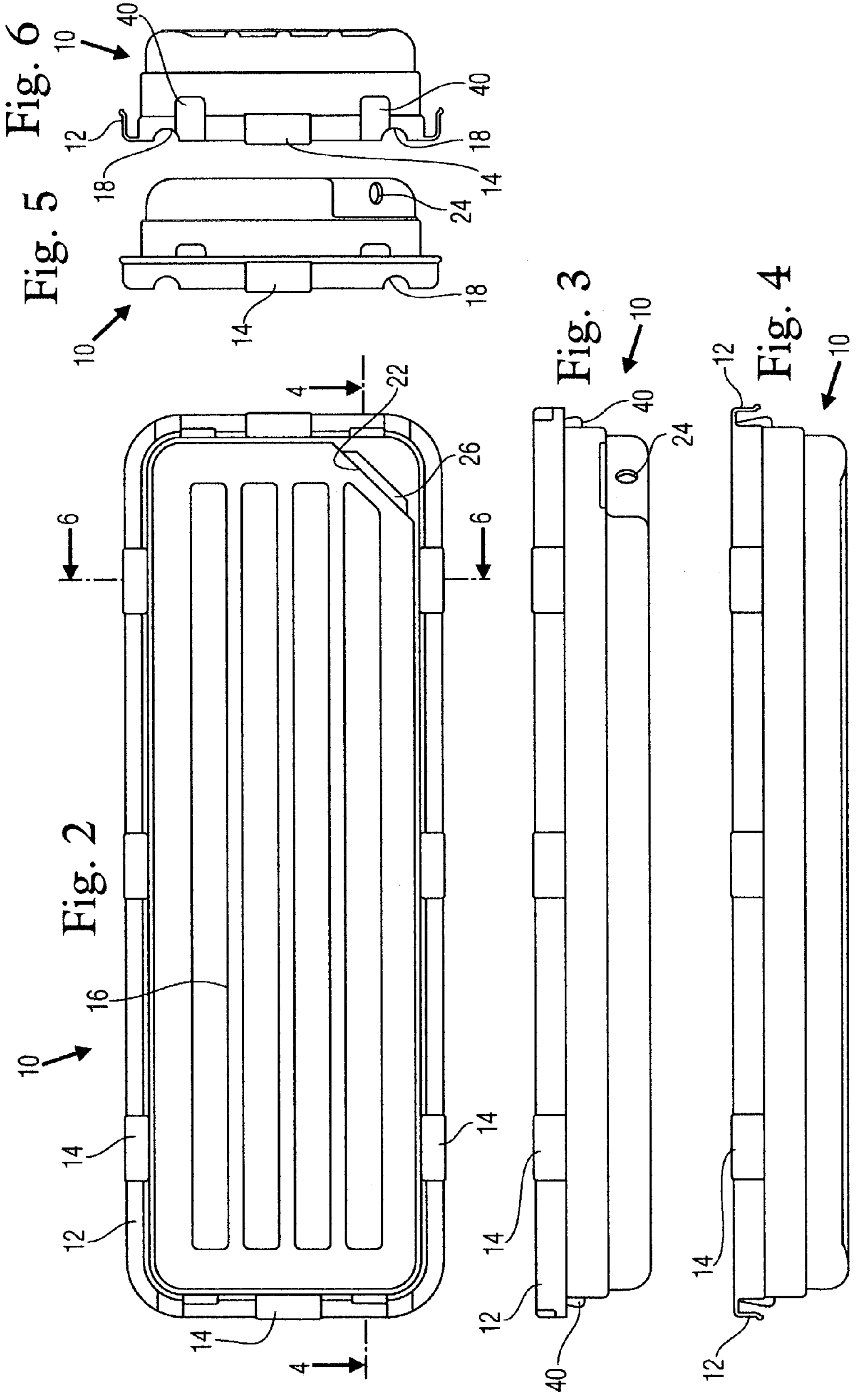
FIG. 2 is a top plan view of the decontamination tub.
FIG. 3 is a side elevation view of the decontamination tub.
FIG. 4 is a cross section view taken across the lines 4—4 of FIG. 1.
FIG. 5 is an end view of the decontamination tub.
FIG. 6 is a cross section view taken across the lines 6—6 of FIG. 1.
Figure 7:
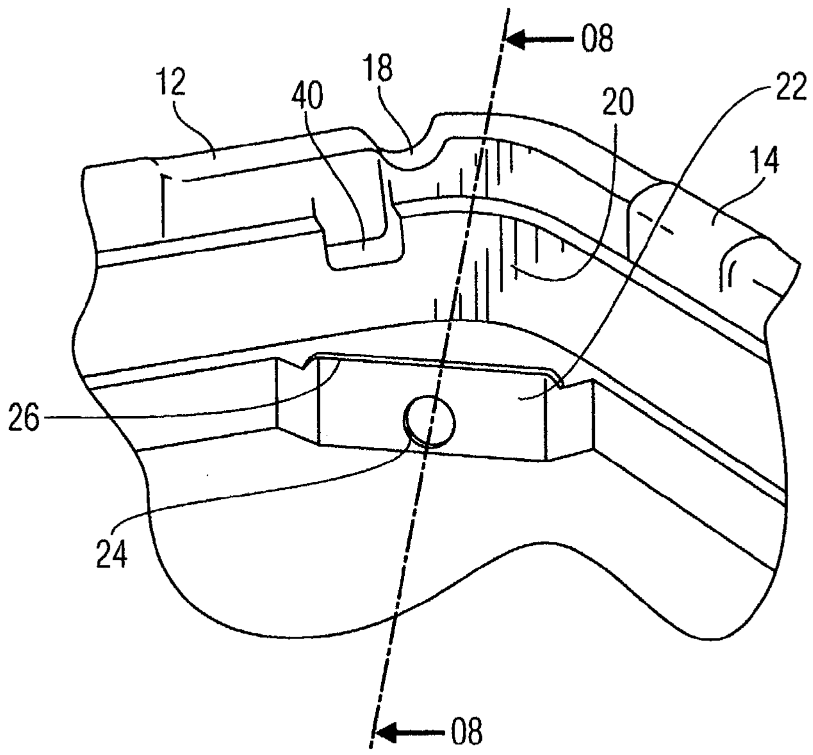
FIG. 7 is an enlarged perspective view of the ledge in a corner of the tub.
Figure 8:
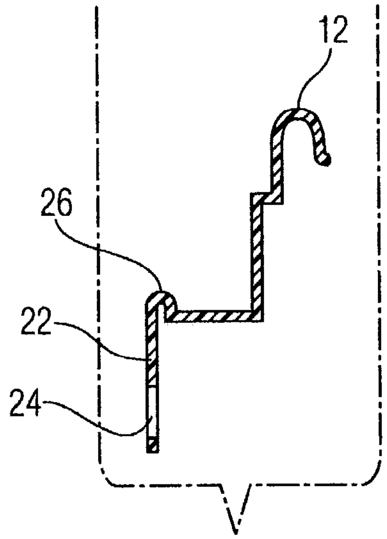
FIG. 8 is a cross section view taken across the lines 8—8 of FIG. 7.

Referring to FIGS. 1–8, a tub 10 is formed from a rigid plastic material such as high density polyethylene. Preferably, the tub 10 is approximately 80 inches long, 30 inches wide and 10 inches deep. An outwardly overhanging lip 12 is formed circumferentially around the tub 10. Spaced apart around the lip 12 are a plurality of grip areas 14 which provide a means for persons to grasp the tub 10 for ease of carrying. Preferably one grip area 14 is formed in at opposite ends of the tub 10 and three grip areas 14 are formed along each side of the tub 10. Approximately three ribs 16 are formed longitudinally on the bottom of the tub 10. Not only do the ribs provide structural strength to the tub 10, but the ribs extend outwardly from the bottom of the tub and serve as a rail for moving the tub on a roller type conveyor as will be explained. In addition, the ribs 16 facilitate drainage of liquids within the tub 10. In each end wall of the tub, there are formed two spaced-apart notches 18. The use of these notches will be discussed.

In one corner 20 of the tub 10, a ledge 22 is formed angularly with respect to the pair of adjoining walls of the tub. Preferably, the angle is 45°. In a molded tub 10, the formation of the internal ledge generates a corresponding external depression in the outer wall of the tub 10. It is also preferred that a ridge 26 be formed on the upper surface of the ledge 28 above the vertical face of the ledge 22. Thus, a space is provided for placement of loose articles which may be associated with the body or body parts.

An opening 24 is formed in the vertical face of the ledge 22 adjacent to the bottom of the tub 10. A drain valve 28 is connected to the opening with a control means outside of the tub 10. In this manner, liquid collected within the tub 10 may be drained from the tub 10.

Figure 9:
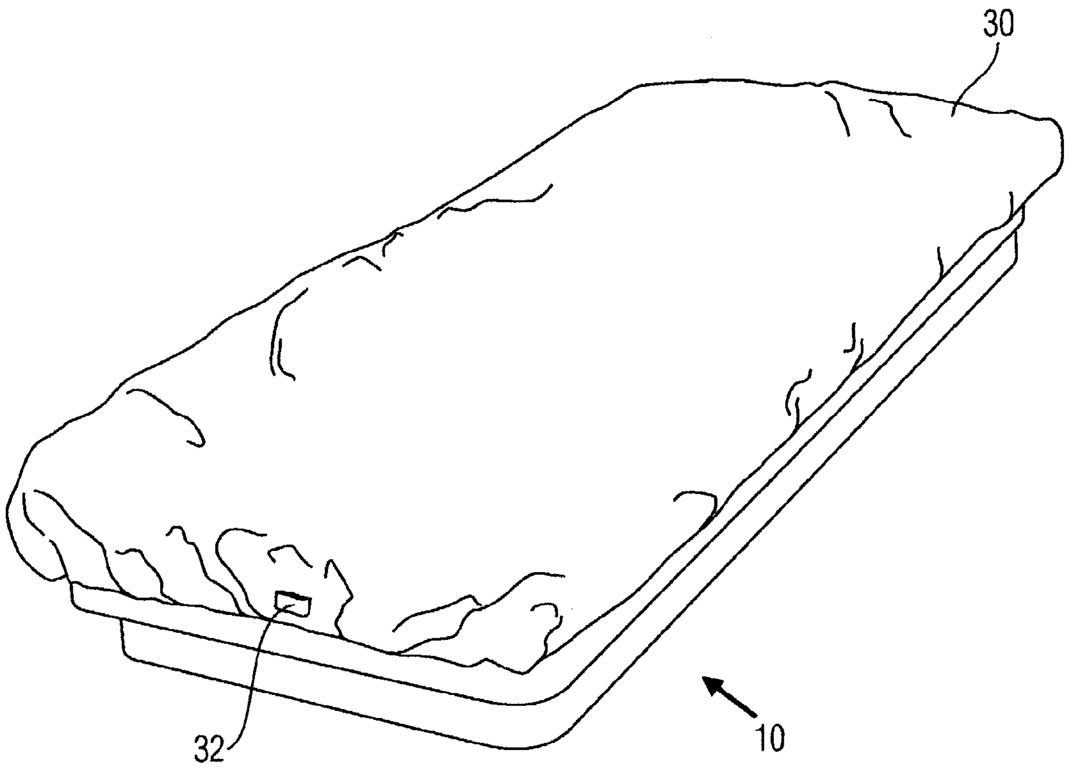
FIG. 9 is a perspective view showing a flexible cover over the decontamination tub.
Figure 10:
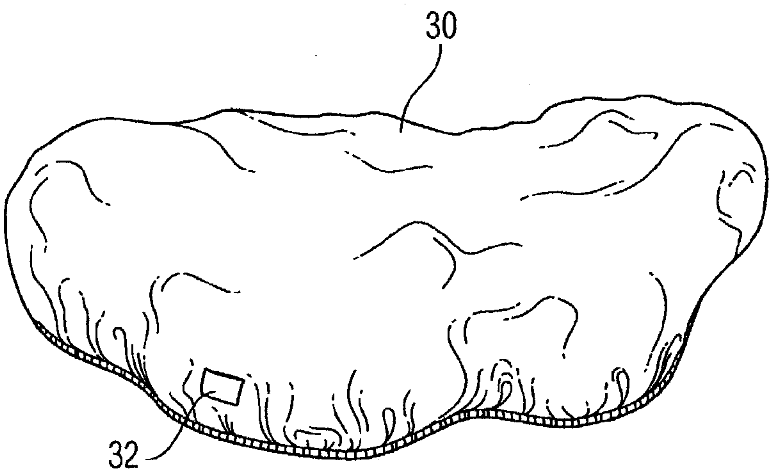
FIG. 10 is a perspective view of flexible cover.

A flexible cover 30 having an elastic band circumferentially thereof is fitted over the open top of the tub as shown in FIGS. 9 and 10. The flexible cover preferably is formed from polyethylene and is water resistant, mildew resistant and treated with an anti-fungal material. The flexible cover fits snugly over the tub 10 and its contents. A transparent pocket 32 is formed on the outside of the cover so that identification or other information may be provided.

Figure 11:
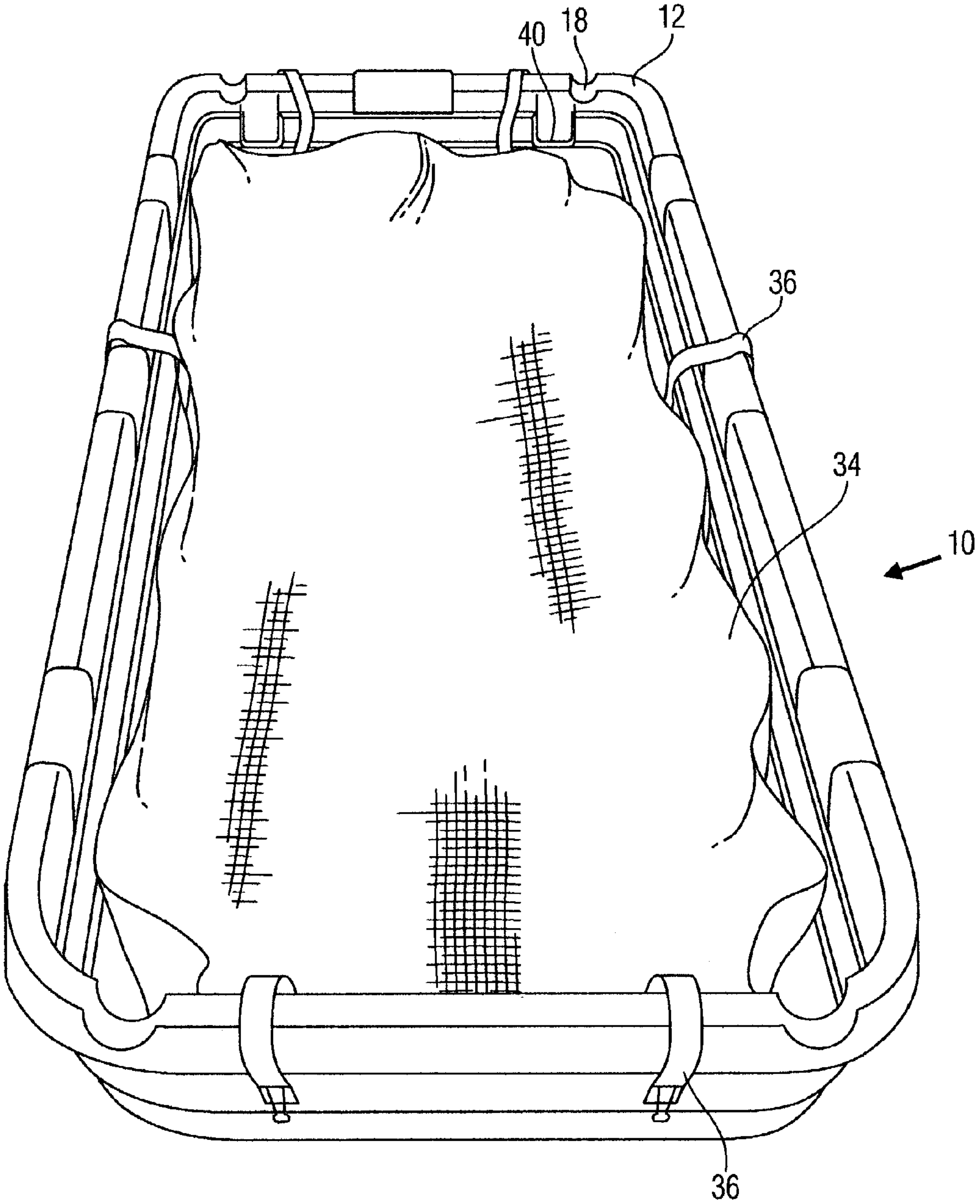
FIG. 11 is a perspective view showing a transfer sheet spread out within the decontamination tub.

As shown in FIG. 11, a transfer sheet 34 is provided and is placed in the tub 10. The transfer sheet 34 is approximately 78 inches long and 24 inches wide and, preferably, is formed of monofilament polypropylene in a basket-type weave. This permits passage of liquid through the transfer sheet 34 and allows complete submersion of a body and/or body parts in the tub 10. Also, the transfer sheet 34 retains items which provides easy collection of trace evidence. A plurality of straps 36 are connected to the transfer sheet 34 to provide a means of holding the transfer sheet 34 containing the body and/or body parts and to dispose the transfer sheet 34 in the tub 10.

Figure 12:
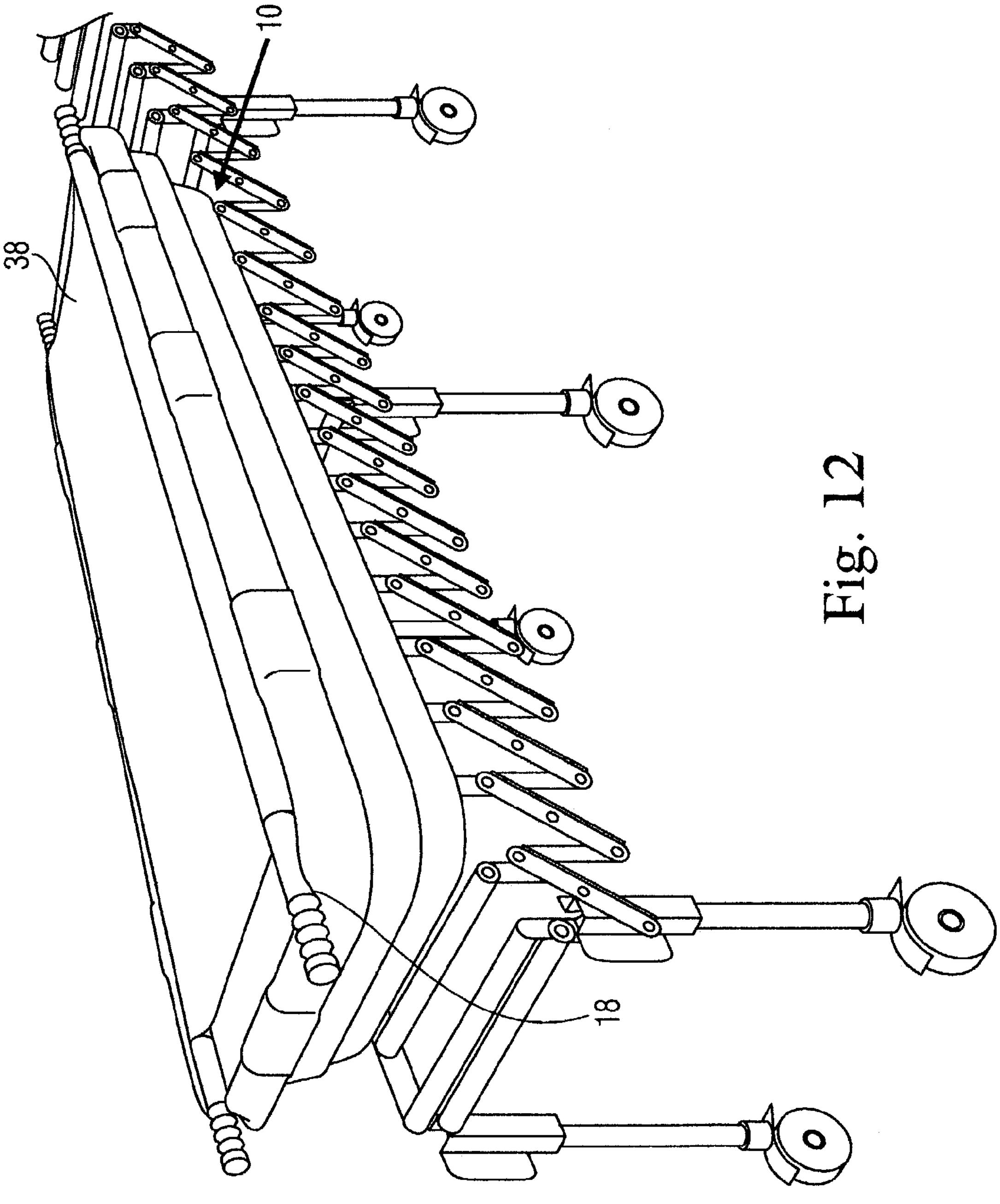
FIG. 12 is a perspective view showing a stretcher disposed on the tub.

A stretcher 38 having four outwardly extending handles is placed on the tub 10 with one handle being received in a respective one of the notches 18 formed on the opposite ends of the tub 10 as shown in FIG. 12. The type of stretcher 38 is not critical, the important factor being that the stretcher, including the handles, is longer than the tub 10 and the handles are spaced apart by a distance equal to the spacing between the notches 18 on the tub 10. It is also advantageous if the bed of the stretcher 38 is made from a mesh material which can withstand decontamination procedures. The Raven® Model 90C Litter sold by North American Rescue Products, Inc., Easely, S.C. has been found to meet the requirements.

Figure 13:
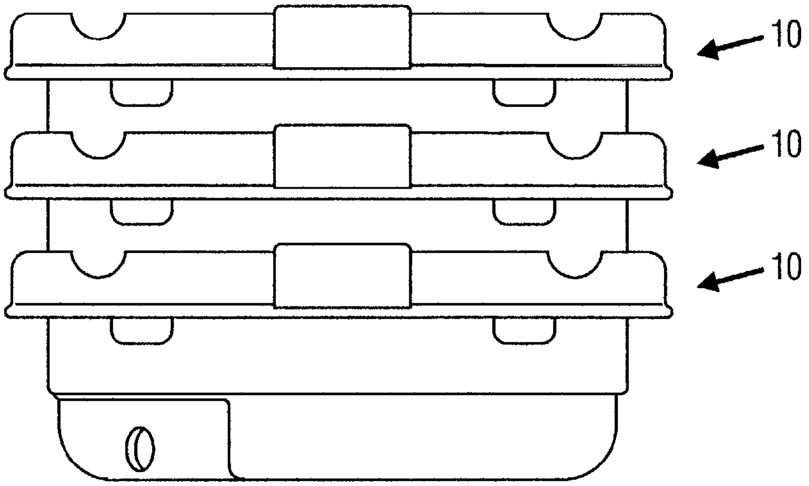
FIG. 13 is a side elevation view showing stacking of the tubs.

As shown in FIG. 13, a plurality of tubs 10 may be stacked or nested vertically for ease of transport and storage. The opposite ends of each tub 10 has two wells 40 formed therein. The wells 40 on two nested tubs 10 abut each other so that the extent of the nesting is limited. The bottoms of the stacked tubs 10 are spaced apart by a predetermined distance.

Figure 14:
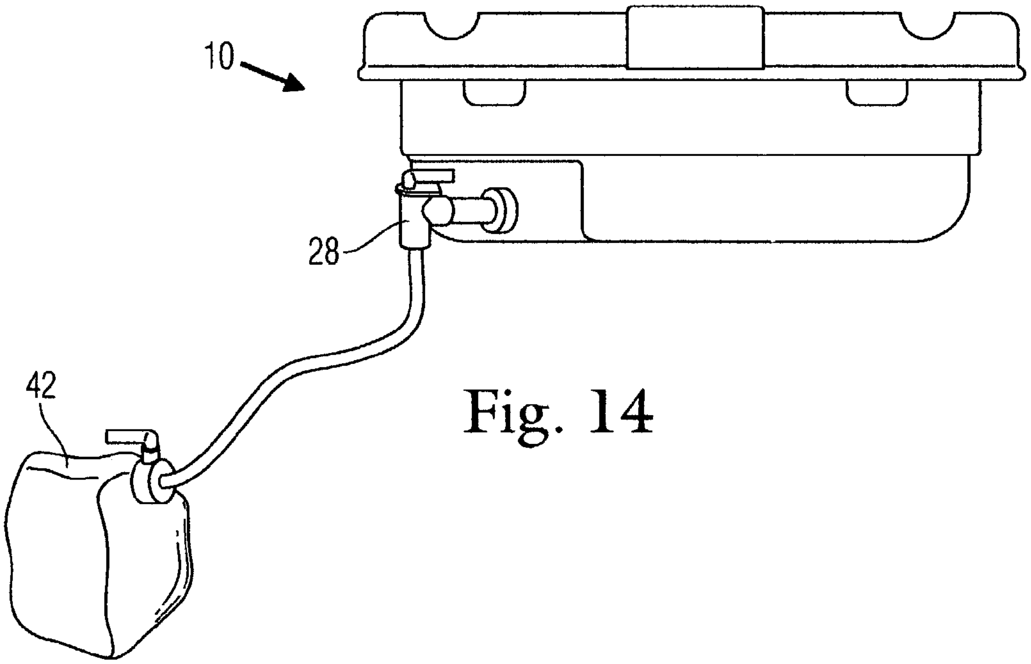
FIG. 14 is a perspective view showing the drain valve on the tub connected to a reservoir.

The drain valve 28 in the tub 10 preferably is connected to a reservoir 42 or other container into which the blood, body fluids and decontamination material may be collected (FIG. 14). The filled reservoirs 42 may be retained for future testing such as DNA or other identification procedures. It is preferred that a collapsible reservoir 42 be used to reduce storage space. Optimally, the filled reservoirs 42 may be moved to other locations for disposal. In extenuating circumstances, the drained fluid from the tub 10 may be directed to a berm or trench.

The decontamination system of the present invention can be used for any situation where there are bodies of victims of war, major accidents or catastrophic events. In some disasters, only body parts may be recovered. In the event of the use of hazardous substances such as chemical or biological agents, such as might occur in a military situation or a terrorist attack, it will be necessary to decontaminate the victims, their clothing and body parts to prevent the production of additional casualties of persons exposed to the contamination.

Persons in protective equipment including gas masks, gloves and protective clothing place the contaminated victims and/or body parts on the transfer sheet 34 or the stretcher 38. The transfer sheet 34 may be placed on the stretcher 38. The carrying means such as the transfer sheet 34 is placed in the tub 10 or the stretcher 38 is rested on the top of the tub 10 with the handles of the stretcher 38 received in the notches 18 in the tub 10. The blood and other body fluids will drain through the porous material of the carrying means into the bottom of the tub 10. The tub 10 should be tilted so that the fluids will collect at the ledge 22 in the one corner 20 of the tub 10 and, if needed, could be drained, through the drain valve 28 located at that corner, into the reservoir 42. The fluids could be marked and placed aside for later identification.

Figure 15:
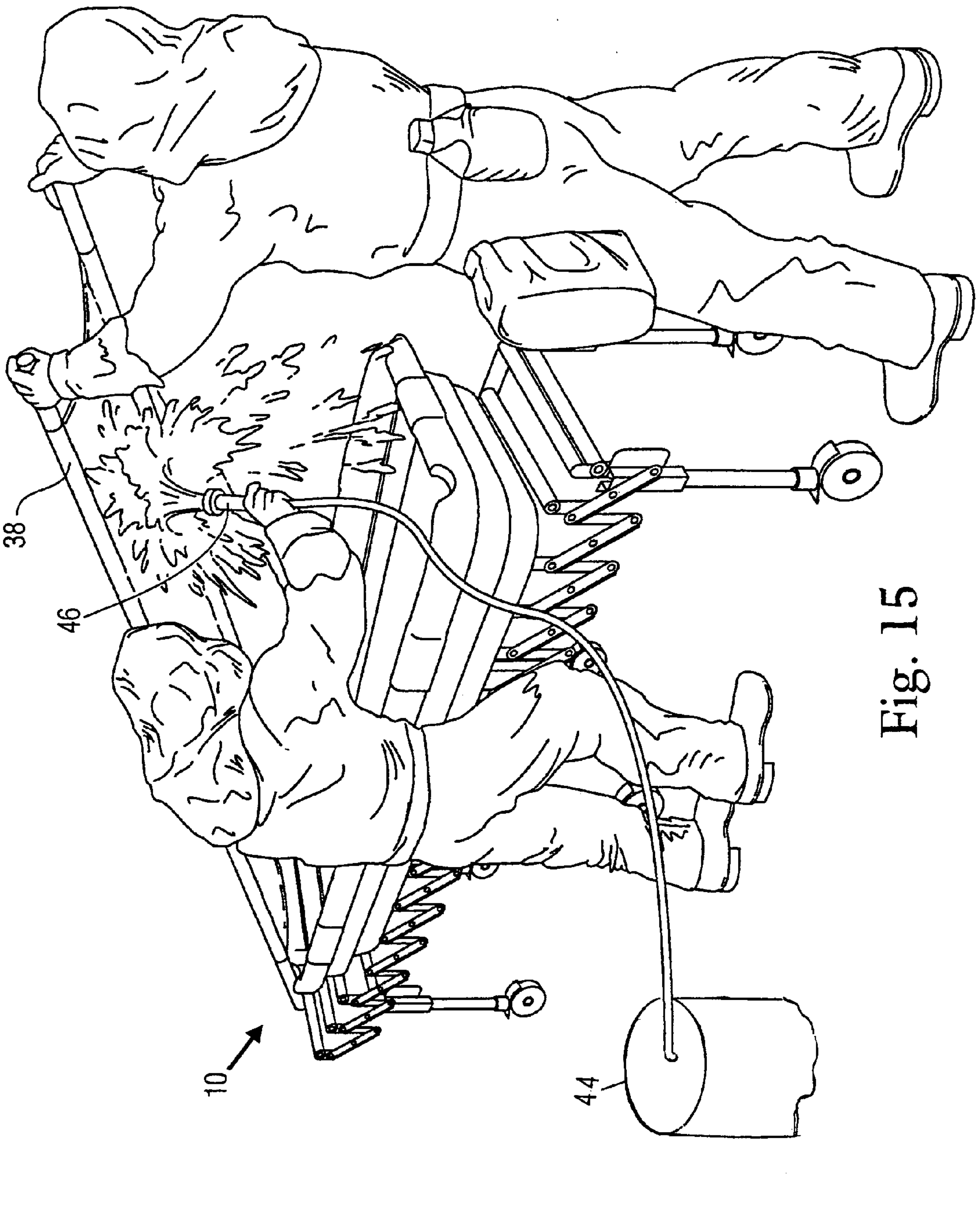
FIG. 15 is a perspective view showing spraying decontaminant on the stretcher over the tub.

The tub with the body/body parts may be placed on a roller system for transport to a decontamination station. The tub 10 may be placed on a litter stand or other support means. If hazardous materials are present, a supply of decontamination medium 44 is connected to a spraying device 46. The decontamination material may be water with detergent or soap or a substance containing active chlorine or an approved decontamination formulation. Preferably, the spraying device 46 is hand held. Personnel in protective gear spray the decontamination material onto the body and/or body parts in the tub 10. As shown in FIG. 15, one end of the stretcher 38 may be lifted to facilitate spraying from all directions. The engagement of the handles of the stretcher 38 in the notches 18 on the tub 10 allows the raising of one end of the stretcher 38 by one person with the other end of the stretcher 38 leveraged against the notches 18. The body fluids, blood and decontamination material are drained from the drain valve 28 into the reservoir 42 after the body and/or body parts are removed. The decontaminated body and/or body parts is then moved to a clear area the body and/or body parts can be removed from the tub 10. In an ongoing operation where there is a limited number of tubs 10, a used tub 10 may be washed with a proper decontaminant and reused.

In situations where there are no hazardous materials, the tub, transfer sheet and stretcher may be used for bodies and/or body parts without the decontamination steps. This use is for events such as industrial accidents, airplane crashes, earthquakes and occasions where there are multiple bodies and/or body parts. The body fluids and/or bodies may be needed for forensic investigation.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A tub for receiving a body and body parts comprising:

the tub having four walls connected to a bottom, forming four corners, a lip formed on each wall distal from the bottom, the walls being formed in a step-shaped manner from the lip to the bottom, the tub being unitary, ribs formed longitudinally on the bottom extending outwardly therefrom, the ribs providing drainage means for collection of blood and body fluids, the tub having four notches formed in the lips of the walls at opposite ends of the tub respectively, wherein a stretcher handle may be received in the notches, the stretcher depending within the tub and the stretcher having the body and body parts resting thereon, a ledge formed in one of the corners of the tub, the ledge being angularly connected to a pair of adjoining walls and having an opening therein, an opening being formed in the one of the walls of the tub and aligned with the opening in the ledge, the opening being adjacent to the bottom of the tub, a valve means being connected to the opening in the ledge, such that a decontamination medium may be introduced into the tub to decontaminate the body and body parts and the blood and body fluids and the decontamination medium may be drained through the valve means.

2. The tub of claim 1, wherein the tub said four notches are located two at each opposite end of the tub, respectively, and wherein a stretcher is received in the notches depending within the tub, and the stretcher having the body and body parts resting thereon.

3. The tub of claim 1, wherein a flexible cover is fitted snugly over the tub.

4. The tub of claim 3, wherein the flexible cover is water resistant and mildew resistant.

5. The tub of claim 1, wherein a reservoir is connected to the valve means to allow collection of blood, body fluids and decontamination medium from the decontamination tub.

6. The tub of claim 5, wherein the reservoir is collapsible.

7. The tub of claim 1, wherein said lips are outwardly overhanging about the tub a plurality of spaced-apart hand grips being formed in the overlapping lip such that the tub may be grasped for carrying.

8. A tub for receiving a body and body parts comprising:

the tub having four walls connected to a bottom, forming four corners, a lip formed on each wall distal from the bottom, the walls being formed in a step-shaped manner from the lip to the bottom, the tub being unitary, ribs formed on the bottom extending outwardly therefrom, the ribs providing drainage means for collection of blood and body fluids, the tub having four notches formed in the lips of the walls at opposite ends of the tub respectively, wherein a stretcher handle may be received in the notches, the stretcher depending within the tub and the stretcher having the body and body parts resting thereon, a ledge formed in one of the corners of the tub, the ledge being angularly connected to a pair of adjoining walls, an opening being formed in one of the walls of the tub, the opening being adjacent to the bottom of the tub, a valve means being connected to the opening, a reservoir connected to the valve means to allow collection of blood, body fluids and decontamination medium from the decontamination tub, an outwardly overhanging lip formed about the tub, a plurality of spaced-apart hand grips being formed in the overlapping lip such that the tub may be grasped for carrying, a flexible cover fitted snugly over the tub, such that a decontamination medium may be introduced into the tub to decontaminate the body and body parts, and blood and body fluids and the decontamination medium may be drained through the valve means.

* * * * *